United States Patent [19]
Bryant, Jr. et al.

[11] Patent Number: 6,096,704
[45] Date of Patent: Aug. 1, 2000

[54] PRO-FRAGRANCE COMPOUND

[76] Inventors: Lonnie Liddell Bryant, Jr.; Robert Ya-Lin Pan, both of c/o Procter & Gamble Far East, Inc., 17, Koyo-cho Naka 1-chome, Higashinada-ku, Kobe 658, Japan

[21] Appl. No.: 09/142,888

[22] PCT Filed: Mar. 21, 1997

[86] PCT No.: PCT/US97/05373

§ 371 Date: Sep. 18, 1998

§ 102(e) Date: Sep. 18, 1998

[87] PCT Pub. No.: WO97/34578

PCT Pub. Date: Sep. 25, 1997

[51] Int. Cl.[7] .............................. A61K 7/46; A61K 7/00; A61K 7/15; C11D 3/50; C07C 13/00
[52] U.S. Cl. ..................... 512/2; 512/3; 512/20; 512/25; 424/401; 424/65; 424/69; 424/47; 424/73; 510/101; 585/24
[58] Field of Search ................... 424/401, 65, 69, 424/47, 73; 512/2, 3, 25, 20; 510/101; 585/24

[56] References Cited

U.S. PATENT DOCUMENTS

| | | | |
|---|---|---|---|
| 3,308,067 | 3/1967 | Diehl | 510/346 |
| 3,664,961 | 5/1972 | Norris | 510/305 |
| 3,779,932 | 12/1973 | Jaggers et al. | 510/102 |
| 3,849,326 | 11/1974 | Jaggers et al. | 510/101 |
| 3,879,425 | 4/1975 | Hall et al. | 549/430 |
| 3,923,700 | 12/1975 | Jaggers et al. | 512/7 |
| 3,932,520 | 1/1976 | Hoffmann | 568/415 |
| 3,947,574 | 3/1976 | Jaggers et al. | 424/600 |
| 4,055,634 | 10/1977 | Brenner et al. | 424/47 |
| 4,144,226 | 3/1979 | Crutchfield et al. | 525/401 |
| 4,702,857 | 10/1987 | Gosselink | 510/299 |
| 4,711,730 | 12/1987 | Gosselink et al. | 510/299 |
| 4,721,580 | 1/1988 | Gosselink | 510/297 |
| 4,877,896 | 10/1989 | Maldonado et al. | 560/14 |
| 4,968,451 | 11/1990 | Scheibel et al. | 510/299 |
| 5,378,468 | 1/1995 | Suffis et al. | 424/401 |
| 5,415,807 | 5/1995 | Gosselink et al. | 8/137 |
| 5,426,095 | 6/1995 | Brunka et al. | 512/12 |
| 5,500,138 | 3/1996 | Bacon et al. | 501/101 |

FOREIGN PATENT DOCUMENTS 02276041  11/1990  Japan .
94/06441  3/1994  WIPO .

*Primary Examiner*—Jill Warden
*Assistant Examiner*—Monique T. Cole
*Attorney, Agent, or Firm*—Richard S. Echler, Sr.; Kim W. Zerby; Jacobus C. Rasser

[57] ABSTRACT

The present invention is directed to a pro-fragrance compound selected from the group consisting of an acetal, a ketal, and mixtures thereof, wherein at least one of a parent aldehyde, ketone, or alcohol of the pro-fragrance acetal or ketal is a fragrance compound, having a ClogP of less than about 4. The ClogP is the logarithm to the base 10 of the octanol/water partition coefficient of the pro-fragrances. Further disclosed are detergent compositions comprising the pro-fragrance compound of the present invention and detersive surfactants.

11 Claims, No Drawings

PRO-FRAGRANCE COMPOUND

FIELD

The present invention relates to an acetal or a ketal pro-fragrance compound.

BACKGROUND

Most consumers have come to expect scented laundry products and to expect that fabrics which have been laundered will also have a pleasing fragrance. It is also desired by consumers for laundered fabrics to maintain the pleasing fragrance over time. Perfume additives may make laundry compositions more aesthetically pleasing to the consumer, and in some cases the perfume imparts a pleasant fragrance to fabrics treated therewith. However, the amount of perfume carry-over from a detergent solution onto a fabric surface is often marginal and does not last long on the fabric surface. In addition, some perfume delivery systems are not stable under alkaline conditions, such as in laundry detergent compositions and detergent solutions. Also, fragrance materials are often very costly. Thus, their inefficient use in detergents and ineffective delivery from detergents to fabric surface usually results in a high cost to both consumers and detergent manufacturers. Industry, therefore, continues to seek more efficient and effective perfume delivery in laundry products.

Acetals and ketals have long been known in perfumery. See Steffen Arctander, "Perfume and Flavor Chemicals," Arctander, N.J., 1969. The majority of these are methyl and ethyl types, and molecular weights may range widely. See, for example, Arctander abstract numbers 6, 11, 210, 651, 689, 1697, 1702, 2480, 2478. However, the known acetals and ketals are generally not desirable for use in laundry products. For 2478, which is phenylacetaldehyde dicitronellyl acetal, molecular weight 414.7, Arctander reports ". . . and it is not exaggerated to say that this acetal is practically abandoned and obsolete in today's perfumery." For 2480, which is phenylacetaldehyde digeranyl acetal, Arctander reports "the title material does not offer substantial advantages or unique odor type and it may be considered of little more than academic interest today." This latter material was still commercially available in 1992 as ROSETAL A (Catalogue, IFF).

Carrier mechanisms for perfume delivery, such as by encapsulation, are also known in the art. See for example, U.S. Pat. No. 5,188,753, issued Feb. 23, 1993.

Early efforts to delay release of perfumes in detergents include the use of certain organometallic compounds, such as titanate or zirconate esters. See U.S. Pat. No. 3,849,326, issued Nov. 19, 1974 and U.S. Pat. No. 3,923,700, issued Dec. 2, 1975. Limited amounts of titanium or zirconium can be useful as catalysts for synthesizing pro-perfume materials.

Personal care compositions, such as deodorant sticks, comprising "body-activated" fragrances are also known. The term apparently refers to the previously known tendency of materials such as acetals derived from perfume alcohols to hydrolyze under acidic pH conditions thereby releasing fragrance. See, for example, U.S. Pat. No. 5,378, 468, issued Jan. 3, 1995 and U.S. Pat. No. 3,932,520, issued Jan. 13, 1976.

Potential fragrance materials for use in such personal care compositions include particular acetals and ketals, exemplified by propylene glycol vanillin acetal. The materials exemplified apparently are rather hydrophilic short chain alcohol or diol derivatives of fragrance aldehydes and upon hydrolysis, deliver one mole of the aldehyde per mole of the potential fragrance material. This development is designed to be incorporated with a personal care product vehicle, resulting in clear deodorant sticks and the like and the compositions containing the potential fragrance materials are applied directly to the substrate (i.e. skin); therefore, the deposition problems resulting from the dilution, rinsing, etc., associated with the laundry process are not at issue.

Factors affecting substantivity of fragrance materials on fabrics are discussed in Estcher et al. JAOCS 71 p. 31–40 (1994).

Laundry detergents are used in dilute aqueous form and contain numerous detergent adjuncts such as synthetic detergents, builders, enzymes and the like which are capable of micellizing, or solubilizing the pro-fragrance. Further, the laundry process includes rinsing, and sometimes drying with tumbling machines after washing. The rinsing tends to remove the useful pro-fragrance material deposited. The tumble-drying further exacerbates the problem of delivering adequate residual fragrance to textile fabric surfaces.

The pro-fragrance compounds of the present invention can be used for a variety of products wherein the conventional fragrances are used. These are, for example, such as shampoos, conditioners, detergent hard surface cleaner, deodorants, cat litter, and the like.

Based on the foregoing, there is a need for a pro-fragrance compound with improved dispersability in aqueous solutions. Especially, pro-fragrance compound used for detergent composition further can be enhanced deposition on fabric surfaces in the wash solution, and enhanced retention on the washed surface during rinsing. None of the existing art provides all of the advantages and benefits of the present invention.

SUMMARY

The present invention is directed to a pro-fragrance compound selected from the group consisting of an acetal, a ketal, and mixtures thereof, wherein at least one of a parent aldehyde, ketone, or alcohol of the pro-fragrance acetal or ketal is a fragrance compound, having a CLogP of less than about 4. The CLogP is the logarithm to base 10 of the Octanol/Water Partition Coefficient of the pro-fragrances.

These and other features, aspects, and advantages of the present invention will become better understood from a reading of the following description, and appended claims.

DETAILED DESCRIPTION

While the specification concludes with claims particularly pointing out and distinctly claiming the invention, it is believed that the present invention will be better understood from the following description.

All percentages and ratios used hereinafter are by weight of total composition, unless otherwise indicated.

All measurements referred to herein are made at 25° C. unless otherwise specified.

All percentages, ratios, and levels of ingredients referred to herein are based on the actual amount of the ingredient, and do not include solvents, fillers, or other materials with which the ingredient may be combined as a commercially available product, unless otherwise indicated.

All publications, patent applications, and issued patents mentioned herein are hereby incorporated in their entirety by reference. Citation of any reference is not an admission regarding any determination as to its availability as prior art to the claimed invention.

As used herein, "comprising" means that other steps and other components which do not affect the end result can be added. This term encompasses the terms "consisting of" and "consisting essentially of."

PRO-FRAGRANCES

As used herein, "pro-fragrance" compound means a compound which may or may not be odoriferous in itself but which, upon hydrolysis, produces a desirable odor which is characteristic of one or more of its hydrolysis products. This term includes mixtures of pro-fragrance compounds and further encompasses the term "pro-perfume." Acetals and Ketals can be considered as derivable from aldehydes or ketones in combination with alcohols. These aldehydes, ketones and alcohols are herein termed "parents" or "parent compounds" of the acetal or ketal. At least one parent of any of the instant acetals or ketals is a fragrance compound.

The pro-fragrance compound of this present invention has CLogP of less than about 4, wherein the CLogP is the logarithm to base 10 of the Octanol/Water Partition Coefficient of the pro-fragrance compound. The pro-fragrances having the CLogP of less than about 4 give good dispersibility in the aqueous solution. Without being bound by theory, it is believed that the CLogP, as described herein, can be lower when the number of alkoxy moiety included in the pro-fragrance compound is increased.

These pro-fragrance compounds can further be characterized as having a molecular weight of at least about 170 and a half-life of less than 60 minutes when measured at pH 0 by the Hydrolysis Half-life (t-½) Test as described herein.

The preferred pro-fragrances can be cyclic or acyclic having at least 3 oxygens. Preferably, the cyclic pro-fragrance compound has at least two alkoxylate moiety and the acyclic pro-fragrance compound has at least 4 alkoxylate moiety.

An important class of the pro-fragrance compounds herein are those derived from a fragrance or non-fragrance alcohol, particularly $C_6$–$C_{20}$ (preferably $C_{11}$–$C_{20}$, more preferably $C_{14}$–$C_{18}$ alcohols) saturated or unsaturated, linear or branched aliphatic alcohols, commonly referred to as detergent alcohols and a fragrant $C_9$- or higher unsaturated aldehyde or a fragrance ketones.

Preferably, parent alcohols of the present invention have at least one alkoxy moiety. Due to increasing the member of alkoxy moiety as described above, the pro-fragrances having the CLogP of less than about 4 give good dispersibility in detergent solution. The preferred parent alcohols can include the alkoxylates of detergent alcohols, mono-alkyl ethers of short-chain polyalkoxylates, polyols including those which are alkoxylated with 1 to 30 groups of ethylene oxide or propylene oxide. Preferred parent aldehydes or ketones herein, will be derived from a parent aldehyde having molecular weight above about 80.

More generally, a wide range of acetals and ketals are included within the invention. Many fragrant aldehydes, ketones, and alcohols which are suitable parents for the present acetals and ketals are known to the art. See, for example, Arctander's compilation referenced hereinabove for fragrant parents. These will be also obtainable commercially from perfume houses such as IFF, Firmenich, Takasago, H&R, Givaudan-Roure, Dragoco, Aldrich, Quest, and others.

Acetals

The pro-fragrances of the present invention include an acetal. The acetal can be used to deliver fragrance aldehydes, fragrance alcohols, or both, preferably to deliver fragrance aldehydes derived from parent aldehydes.

Acetals suitable in the present invention include the following structure:

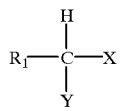

X and Y are derived from a starting alcohol and $R_1$ and the H is derived from a starting aldehyde.

X and Y in the above general structure which can be either fragrant alcohols or non-fragrant alcohols includes variable alkoxy moieties. X and Y can be the same or different allowing the delivery of more than one type of fragrant alcohol. When the alcohols are non-fragrant alcohols, it is preferred that they are $C_6$–$C_{20}$ alcohols, especially fatty alcohols, which may optionally be modified by ethoxylation or propoxylation. X and Y can be simple alcohols containing a single OH group, or can be polyols containing 2 or more OH groups, more preferably, diols.

In general, alcohols can be saturated, unsaturated, linear or branched, alkyl, alkenyl, alkylaryl, alkylalkoxylate derivatives with one or more alcohol groups. The alcohols may contain additional functionality such as amines, amides, ethers, or esters as a part of their structure.

Preferably, the acetal of the present invention can be cyclic or acyclic, and may contain one or more acetal groups through derivatizing one or more aldehydes. The terms cyclic and acyclic in this context refers to the presence or absence of a covalent bond connecting moieties X and Y of the acetal. X and Y of the cyclic acetals form a ring structure and have at least two alkoxylate moieties. The preferred acyclic acetals having at least four alkoxylate moieties incorporate linear alcohols.

The cyclic acetals are derived from polyols. Preferred polyols include those which are alkoxylated with 1 to 30 units of ethylene oxide or propylene oxide. Nonlimiting examples of the polyols include, for example, sorbitol, glucose, sucrose, and other saccharides.

The acyclic acetals are derived from mono-alcohols. Preferred mono-alcohols containing a single OH group can include the alkoxylates of detergent alcohols and mono-alkyl ethers of short-chain polyalkoxylates. Preferably, the mono-alkyl ethers of short-chain polyalkoxylates include $C_1$–$C_5$ alkyl moiety. Nonlimiting examples of the parents alcohols include ethyl alcohol, propyl alcohol, butyl alcohol, lauryl alcohol, and myristyl alcohol.

$R_1$ and the H of the above general structure are is derived from a starting aldehyde. In general, both fragrant and non-fragrant aldehydes incorporated into the instant acetals can be aliphatic, allylic or benzylic. The aldehydes can be saturated, unsaturated, linear, branched, or cyclic. The structures can include alkyl, alkenyl, or aryl moieties, as well as additional functional groups such as alcohols, amines, amides, esters, or ethers.

Preferably, acetals herein, will be derived from a parent aldehyde having molecular weight above about 80.

Many fragrant aldehydes and alcohols which are suitable parents for the present acetals and ketals are known to the art. See, for example, Arctander's compilation referenced hereinabove for fragrant parents. Nonlimiting examples of the fragrant parent aldehydes include but are not limited by the following examples: hydratropaldehyde, p-t-bucinal, Floralozone™, phenylpropanal, anisaldehyde, cymal, cyclamal, triplal, helional, hexylcinnamic aldehyde, vanillin, ethyl vanillin, citral, ethyl citral, citronellal, methyl octyl acetaldehyde, methyl nonyl acetaldehyde, octanal, decanal, dodecanal, lauric aldehyde, chrysanthal, isosyslocitral, melonal, trans-4-decenal, adoxal, hydroxycitronellal, and iso-hexenyl cyclohexenyl carboxaldehyde.

Specific preferred pro-fragrance acetal compounds are nonlimitingly illustrated by the following:

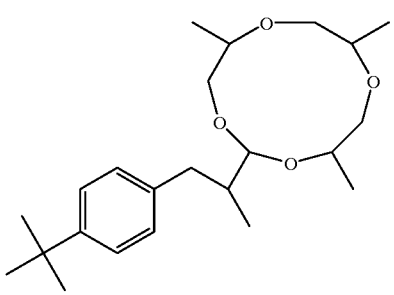

which is derived from P.T. Bucinal and tripropylene glycol. Also preferred is

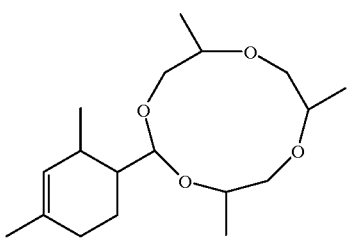

which is derived from cyclal c and tripropylene glycol.
Some specific examples of acyclic acetals useful herein include:

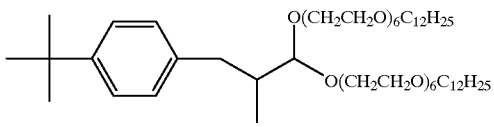

which is derived from P.T. Bucinal and Neodol 6–25 an admixture of $C_{12}$ and $C_{15}$ alkyl chains (thereby the "25") which are ethoxylated to an average of 6 ethyleneoxy units (thereby the "6")) and

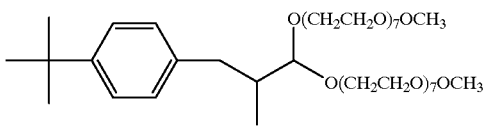

which is derived from P.T. Bucinal and PEG-300 methyl ether.

Additionally, suitable acetals herein are cyclic acetals derived from the reaction of fragrance aldehydes with polyhydroxyglucosides, including the polyhydroxyamides. Typical examples of suitable polyhydroxy amides include the $C_{12}$–$C_{18}$ N-methylglucamides. See WO 9,206,154. Other sugar-derived acetal or ketal parent compounds herein include the N-alkoxy polyhydroxy fatty acid amides, such as $C_{10}$–$C_{18}$ N-(3-methoxypropyl) glucamide.

Ketals

The pro-fragrance compound of the present invention includes a ketal. The ketal can be used to deliver a fragrance ketone. The discussion for the ketals herein can be constructed using structural principles analogous to those used in discussing acetals supra.

Ketals suitable in the present invention include the following structure:

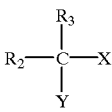

X and Y are derived from alcohols or polyols and $R_2$ and $R_3$ are derived from the parent ketone, and can be the same or different.

As noted in defining the acetals supra, X and Y for Ketals in the above general structure which can be either fragrant alcohols or non-fragrant alcohols including variable alkoxy moieties. The parent alcohols for the ketals can include, but are not limited to, those described as the parent alcohols of the acetals in the section of acetals.

In general, alcohols can be saturated, unsaturated, linear or branched, alkyl, alkenyl, alkylaryl, alkylalkoxylate derivatives with one or more alcohol groups. The parent alcohols may contain additional functionality such as amines, amides, ethers, or esters as a part of their structure.

$R_2$ and $R_3$ of the above general structure are derived from the parent ketone. In general, both fragrant and non-fragrant ketones can be aliphatic, allylic or benzylic. The ketones can be saturated, unsaturated, linear, branched, or cyclic, preferably including alkyl, alkenyl, or aryl moieties as well as other functional groups including amides, amines, ethers, or esters.

Preferably, ketals herein, will be derived from a parent ketone having molecular weight above about 80.

Nonlimiting examples of the parent ketones include, for example, irone alpha, alpha-ionone, beta-ionone, gamma-methyl ionone, methyl beta-naphthyl ketone, cis-jasmone, damascenone, alpha-damascenone, benzylacetone, methyl dihydrojasmonate, methyl amyl ketone, methyl heptyl ketone, methyl hexyl ketone, methyl nonyl ketone, carvone, cassione, menthone, and geranylacetone. Other suitable ketones include diketones, e.g. 2,4-pentadione.

The non-fragrant ketone can contain one or more ketone functional groups and such groups can be further derivatized so that the ketal is polymeric. While polyketals are included herein, they are less preferred than mono- and di-ketals. Monoketals are most preferred.

Specific preferred pro-fragrance ketal compounds are nonlimitingly illustrated by the following:

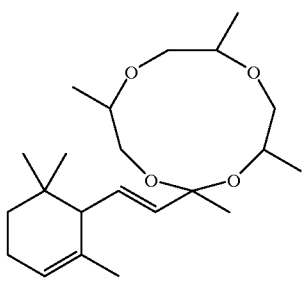

which is derived from alpha-ionone and tripropylene glycol.
Some specific examples of acyclic ketals useful herein include:

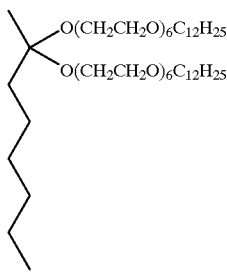

which is derived from 2-octanone and Neodol 6–25 can admixture of $C_{12}$ and $C_{15}$ alkyl chains (thereby the "25") which are ethoxylated to an average of 6 ethyleneoxy units (thereby the "6")) and

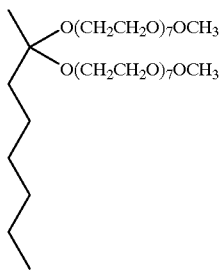

which is derived from 2-octanone and PEG-300 methyl ether.

The pro-fragrance compounds of the present invention can be used for a variety of products wherein the conventional fragrances are used. These are, for example, such as shampoos, conditioners, detergent hard surface cleaner, deodorants, cat litter, and the like.

Synthesis of Pro-fragrances

Acetals and ketals can be prepared by the acid-catalyzed reaction of an aldehyde or ketone with an alcohol (or diol), using conventional acid catalysis such as HCl or p-toluenesulfonic acid, or supported sulfonic acid catalysts e.g., AMBERLYST 15™. See Meskens, F., *Synthesis*, (7) 501 (1981) and Meskens, F., *Jannsen Chim Acta* (1) 10 (1983). Many aldehyde, ketone and alcohols useful in the synthesis of acetal and ketal pro-fragrances of the present invention are sensitive to strong acid conditions and can undergo undesirable side reactions. See Bunton, C. A. et al, *J. Org. Chem.* (44), 3238, (1978), and Cort, O., et al, *J. Org. Chem.* (51), 1310 (1986). It is also known that acetals of alpha, beta-unsaturated aldehydes can undergo migration of the double bond under the inappropriate selection of the acid catalyst. See Meskens, F., *Synthesis*, (7), 501, (1981) and Lu, T.-J, et al. *J. Org. Chem.* (60), 2931, (1995). For acid sensitive materials, acid catalysts with pka's among 3 and 4 are the most desirable to minimize double bond migration while maintaining the reactivity necessary to produce the acetal (or ketal). For example, in the synthesis of digeranyl decanal, p-toluenesulfonic acid ($pK_a$=1) causes undesirable side reactions with geraniol. Citric acid ($pK_{a1}$=3.1, $pK_{a2}$=4.8, $pK_{a3}$=6.4) can be used to form the acetal without side reactions.

Another technique of avoiding side reactions in preparing acetals and ketals of acid sensitive material, such as geraniol, is by transacetalization of a dimethyl acetal or ketal with a higher molecular weight alcohol, using a mild Lewis acid such as titanium isopropoxide or boron trifluoride etherate as the catalyst.

TEST METHODS

Calculation of CLogP

The pro-fragrances of the invention are characterized by their octanol/water partition coefficient P. The octanol/water partition coefficient of a pro-fragrance is the ratio between its equilibrium concentration in octanol and in water. Since the partition coefficients of the pro-fragrance compounds are large, they are more conveniently given in the form of their logarithm to the base 10, logP.

The logP of many compounds have been reported; for example, the Pomona92 database, available from Daylight Chemical Information Systems, Inc. (Daylight CIS), contain many, along with citations to the original literature.

However, the logP values are most conveniently calculated by the "CLOGP" program, also available from Daylight CIS. This program also lists experimental logP values when they are available in the Pomona92 database. The "calculated logP" (CLogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990). The fragment approach is based on the chemical structure of a compound and takes into account the numbers and type of atoms, the atom connectivity, and chemical bonding. The CLogP values, which are the most reliable and widely used estimates for this physicochemical property, can be used instead of the experimental logP values in the selection of pro-fragrances.

Determination of Hydrolysis Half-life (t-½)

Hydrolysis half-life is the measurement used to determine the ease with which the pro-fragrance compound undergoes acid hydrolysis and thereby releases its fragrance component (s) upon exposure to acid conditions. The pro-fragrance compounds of the invention have a half-life of less than 60 minutes, under the described hydrolysis conditions at pH 0. Preferably, pro-fragrances of the invention have a half-life at pH 2 of less than 60 minutes. For granular detergents, the more reactive pro-fragrances, that is, those with half-life at pH 2 of less than one minute, are most suitable, although those having a half-life of less than 60 minutes at pH 0 are also useful. For liquid detergent applications, pro-fragrances having a half-life of less than 60 minutes at pH 0, and half-life greater than one minute at pH 2 should preferably be used.

Hydrolysis half-life is determined by UV/V is spectroscopy in a 90/10 dioxane/water system at 30° C. by following the appearance of the carbonyl absorbance. Because of the hydrophobicity of the pro-fragrance compounds of the invention, a high dioxane/water ratio is needed to ensure solubility of the pro-fragrance. The pH of the water used is achieved by using aqueous HCl. The concentration of the pro-fragrance in the dioxane/water system can be adjusted to achieve convenient, measurable absorbance changes.

All measurements are carried out using a Hewlett Packard 8452 A Diode Array Spectrophotometer using quartz 1 cm path length cuvette cells. Materials used include 1,4-dioxane HPLC Grade 99.9% (Sigma-Aldrich), 1N HCl volumetric solution (J. T. Baker), deionized water filtered with MilliQ-Plus (Millipore) at resistivity of 18.2M Ohm cm. The pH's are measured using an Orion 230 A standardized with pH 4 and pH 7 buffers. The 1N HCl standard is used directly for pH 0 conditions. For pH 2 conditions, 1N HCl is diluted with deionized water.

Pro-fragrance is weighed out in a 10 ml volumetric flask using an analytical balance (Mettler AE 200) Precision is ¹⁄₁₀ mg. The weighed material is dissolved in about 8 ml dioxane. Both the dioxane solution of pro-fragrance and aqueous acid solution prepared as described supra are preheated in their separate containers to a temperature of 30±0.25° C. by means of a water-bath. 1.000 ml of aqueous acid solution is added to the pro-fragrance solution by means of an Eppendorf pipetter. This is followed by diluting to the 10 ml mark with dioxane. Hydrolysis time is measured, starting upon addition of the acid. The pro-fragrance solution is mixed for 30 seconds by shaking, and the solution is transferred to a quartz cuvette. The absorbance of the pro-fragrance solution ($A_t$) is followed at a regular series of time intervals, and the cuvette is kept in the water-bath at the above-indicated temperature between measurements. Initial absorbance ($A_o$) measurements are carried out using an equal concentration of pro-fragrance in a 90/10 v/v dioxane—deionized water solution, and final absorbance ($A_f$) measurements are taken using the hydrolyzed pro-fragrance solution after the hydrolysis is complete. The wavelength at which the hydrolysis is followed is chosen at the wavelength of the absorbance maximum of the parent aldehyde or ketone.

Reaction half-lifes are determined using conventional procedures. The observed first-order rate constant ($k_{obs}$) is determined by slope of the line provided by plotting the following function vs time (min):

$$\text{Ln}\,[(A_o-A_f)/(A_t-A_f)]$$

wherein said function is the natural log of the ratio between the absorbance difference at initial time ($A_o$) and final time ($A_f$) over the absorbance difference at time t ($A_t$) and final time ($A_f$).

Half-life as defined herein is the time required for half of the pro-fragrance to be hydrolyzed, and is determined from the observed rate constant ($k_{obs}$) by the following function:

$$\text{Ln}\,(\tfrac{1}{2})=-k_{obs}\,t\,\tfrac{1}{2}$$

DETERGENT COMPOSITION

The pro-fragrance compound of the present invention can be used for a detergent composition. Preferably, the pro-fragrance acetal, ketal or mixture thereof can be formulated in the detergent compositions at levels in the general range about 0.0001% to about 10%, more preferably from about 0.001% to 5%, more preferably still, from about 0.01% to about 1%.

The pro-fragrance compounds are stable under pH conditions encountered in the formulation and storage of detergent products which have a pH of from about 7.1 to about 13, and during solution-use of such products. Due to hydrophilicity and high degree of heteroatom incorporation, these pro-fragrance compounds give reasonably good deposition from a laundering solution onto fabrics. Because the pro-fragrance compounds are subject to hydrolysis when the pH is reduced, they hydrolyze to release their component fragrance compounds when the fabrics (or other surface) upon which they have been deposited are exposed even to reduced pH such as is present in rinse water, air and humidity. Such a reduction in pH should be at least about 0.1, preferably at least about 0.5 units. Preferably the pH is reduced by at least about 0.5 units to a pH of about 7.5 or less, more preferably about 6.9 or less. Preferably, the solution in which the fabric (or other surface) is washed is alkaline.

The pro-fragrance compound can be used as the sole fragrance compound of the present detergent compositions, or in combination with other pro-fragrances and/or in combination with other fragrance materials, extenders, fixatives, diluents and the like. For example, incorporation of the pro-fragrance material into a waxy substance, such as a fatty triglyceride, may further improve storage stability of the present pro-fragrance compounds in granular laundry detergents, especially those comprising bleaches. In liquid or gel forms of detergent compositions, hydrophobic liquid extenders, diluents or fixatives can be used to form an emulsion wherein the pro-fragrance compound is further stabilized by separating it from the aqueous phase. Nonlimiting examples of such stabilizing materials include dipropylene glycol, diethyl phthalate and acetyl triethyl citrate. Just as there exist hydrophobic perfumery ingredients which can be used to stabilize the pro-fragrance material, there also exist detergency ingredients which also have a perfume stabilizing effect and can be formulated with the pro-fragrance material. Such ingredients include fatty acid amines, low foaming waxy nonionic materials commonly used in automatic dishwashing detergents, and the like. In general, where pro-fragrances are used along with other fragrance materials in detergent compositions herein, it is preferred that the pro-fragrance be added separately from the other fragrance materials.

Detersive Surfactants

The detergent surfactant can further be used for the detergent composition in addition to the pro-fragrance compounds of this invention. Preferably, compositions incorporating synthetic detergent surfactants have a detergent level of from about 0.5% to about 50%, by weight. Compositions containing soap preferably comprise from about 10% to about 90% soap.

Many detergent surfactants which are conventinal for detergent surfactants can be used. Mixtures of anionic and nonionic surfactants are especially useful. Other conventional useful surfactants are listed in standard texts. See also U.S. Pat. No. 3,664,961, issued May 23, 1972.

The detergent compositions herein, preferably, have a pH of from about 7.1 to about 13, more typically from about 7.5 to about 9.5 for liquid detergents and from about 8 to about 12 for granular detergents when measured at 1% concentration of the distilled water at 20° C.

Additional Detergent Ingredients

In addition to the pro-fragrance compounds herein may further include one or more additional detergent ingredients, commonly used in detergent products, such as materials for assisting or enhancing cleaning performance, treatment of the substrate to be cleaned, or to modify the aesthetics of the detergent composition (e.g., conventional perfumes, colorants, dyes, etc.). Such additional ingredients are known to those of skill in the art. The following are illustrative examples of other detergent ingredients.

Builders—Detergent builders can optionally be included in the compositions herein to assist in controlling mineral hardness and in the removal of particulate soils. Suitable builders include those of U.S. Pat. No. 3,308,067, issued Mar. 7, 1967; 4,144,226, issued Mar. 13, 1979 and 4,246,495, issued Mar. 27, 1979. Inorganic as well as organic builders can be used.

The level of builder can vary widely depending upon the end use of the composition and its desired physical form. When present, the compositions will typically comprise at least about 1% builder. Prferebly, liquid formulations typically comprise from about 5% to about 50%, and granular formulations typically comprise from about 10% to about 80%. Lower or higher levels of builder, however, are not meant to be excluded.

Soil Release Agents—Soil Release agents are desirably used in laundry detergents of the instant invention. Suitable soil release agents include those of U.S. Pat. No. 4,968,451, issued Nov. 6, 1990; the nonionic end-capped 1,2-propylene/polyoxyethylene terephthalate polyesters of U.S. Pat. No. 4,711,730, Dec. 8, 1987; the partly- and fully-anionic-end-capped oligomeric esters of U.S. Pat. No. 4,721,580, issued Jan. 26, 1988; the nonionic-capped block polyester oligomeric compounds of U.S. Pat. No. 4,702,857, issued Oct. 27, 1987; and the anionic, especially sulfoaroyl, end-capped terephthalate esters of U.S. Pat. No. 4,877,896, issued Oct. 31, 1989. Another preferred soil release agent is a sulfonated end-capped type described in U.S. Pat. No. 5,415,807.

Other Ingredients

The compositions herein can contain other ingredients such as enzymes, bleaches, fabric softening agents, dye transfer inhibitors, suds suppressors, and chelating agents, all well known within the art.

Formulation with Detergents With or Without Conventional Perfumery Materials

While the pro-fragrances of the present invention can be used alone and simply mixed with essential detergent ingredient, most notably surfactant, they can also be desirably combined into three-part formulations which combine (a) a non-fragrance detergent base comprising one or more synthetic detergents, (b) one or more pro-fragrance acetals or ketals in accordance with the invention and (c) a fully-formulated fragrance. The latter provides desirable in-package and in-use (wash-time) fragrance, while the pro-fragrance provides a long-term fragrance to the laundered textile fabrics. It is preferred that the pro-fragrance compound be added separately from the conventional fragrances to the detergent compositions.

Formulation with other Special-Purpose Fragrance Delivering Compounds

Detergents in accordance with the present invention may further, optionally, if desired, contain other known compounds having the capability to enhance substantivity of a fragrance. Such compounds include, but are not limited to, the aluminum alkoxides such as isobutylaluminium diferanylate as disclosed in U.S. Pat. No. 4,055,634, issued Oct. 25, 1977; or the known titanate and zirconate esters or oligoesters of fragrant materials such as those disclosed in U.S. Pat. No. 3,947,574, issued March 30, 1976 and U.S. Pat. No. 3,779,932, issued Dec. 18, 1973. When using such organoaluminium, organotitanium or organozinc derivatives, they may be incorporated into the detergent compositions of the present invention described herein at their art-known levels.

Methods of Use

In its method aspect, the present invention can be described as:

A method of delivering residual fragrance to a washed surface which comprises the steps of (a) washing said surface in an aqueous solution of a detergent composition comprising a pro-fragrance compound selected from the group consisting of an acetal, a ketal, and mixtures thereof, wherein the pro-fragrance compound having a Clop of less than about 4 and a detersive surfactant, wherein said detergent composition has a pH of at least 7.1 when measured as a 1% solution in distilled-water at 20° C.;

(b) subsequently exposing said surface to a reduction in pH.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

The detergent compositions shown below can be prepared by any conventional method well known in the art. A suitable method and formulation are as follows:

Example 1

[Preparation of Di(Neodol 23-6.5) P.T. Bucinal Acetal by Acid Catalysis]

A 200 ml single necked, round bottom flask is prepared. A 4.09 g portion of P.T. Bucinal (20 mmol), 60 ml of benzene, 22.5 g of Neodol 23-6.5 (50 mmol), and 0.2 g of p-toluene sulfonic acid monohydrate (1 mmol, 5 mol %) is added. The vessel is fitted with a Dean-Stark trap and condenser, and is heated to reflux. The reaction is continued until an equivalent of water is collected in the Dean-Stark trap. Upon cooling, the reaction mixture is washed several times with saturated sodium carbonate and water followed by drying with sodium sulfate. The solvent is removed in vacuo and unreacted parent aldehyde is removed under bulb-to-bulb distillation at 250° C., 0.2 mmHg to yield 19.6 g of pale brown oil (80%) identified spectroscopically at the desired material. The Clop of resulting acetal is less than 4.

Example 2

[Preparation of Tripropylene glycol P.T. Bucinal Acetal by Acid Catalysis]

A 200 ml single necked, round bottom flask is prepared. A 4.09 g portion of P.T. Bucinal (20 mmol), 60 ml of benzene, 4.81 g of tripropylene glycol (25 mmol), and 0.2 g of p-toluene sulfonic acid monohydrate (1 mmol, 5 mol %) is added. The vessel is fitted with a Dean-Stark trap and condenser, and is heated to reflux. The reaction is continued until an equivalent of water is collected in the Dean-Stark trap. Upon cooling, the reaction mixture is washed several times with saturated sodium carbonate and water followed by drying with sodium sulfate. The solvent is removed in vacuo and unreacted parent aldehyde is removed under bulb-to-bulb distillation at 250° C., 0.2 mmHg to yield 6.1 g of pale brown oil (80%) identified spectroscopically at the desired material. The Clop of resulting acetal is less than 4.

Example 3

[Granular Laundry Composition delivering from Di(Neodol 23–6.5) P.T. Bucinal Acetal]

| | |
|---|---|
| Pro-fragrance of Example 1 | 1.0% |
| C11–C13 Dodecyl Benzene Sulfonate | 21.0% |
| C12–C13 Alkyl Ethoxylate EO 1–8 | 1.2% |
| Sodium Tripolyphosphate | 35.0% |
| Zeolite Na 4A | 14.0% |
| Sodium Silicate 2.0 ratio | 2.0% |
| Sodium Carbonate | 23.4% |
| Enzyme (Savinase ™ and/or Lipolase ™ from Novo) | 1.4% |
| Carboxymethyl Cellulose | 0.3% |
| Anionic Soil Release Agent *1 | 0.3% |
| Brightener | 0.2% |
| Silicone Suds Suppressor (Dow Corning Corp) | 0.2% |
| Perfume*2 | 0.3% |
| Sodium Sulfate | 0.5% |
| Moisture balance up to 100% | |

*1See U.S. Pat. No. 4,968,451
*2Perfume composition of the following formula:

| | |
|---|---|
| Benzyl salicylate | 20% |
| Ethylene brassylate | 20% |
| Galaxolide (50% soln. in benzyl benzoate) | 20% |
| Hexyl cinnamic aldehyde | 20% |
| Tetrahydro linalool | 20% |
| | 100% |

Example 4
[Laundry Detergent Comprising Pro-Fragrance and Fully-Formulated Perfume Composition having a Conventional Ketal fragrance Component]

A laundry detergent composition is prepared by weighing 98 g of laundry detergent according to Example 4 with the exception that perfume and pro-fragrance are not included; admixing to said composition 2 g of a perfume of flowery-woody type made up of a mixture of a first premix and a conventional ketal (not in accordance with essential pro-fragrance as defined herein) as follows:

| First Premix: | |
| --- | --- |
| Oil of bergamot | 7.5 g |
| Linalool | 4.0 g |
| Phenyl ethyl alcohol | 4.0 g |
| Benzyl acetate | 2.0 g |
| Citronellol | 0.5 g |
| Hedione ™ (a) | 10.0 g |
| Lyral ™ (b) | 4.0 g |
| Hydroxycitronellal | 2.5 g |
| Rose oxide 1 (c) 10% in DPG | 2.5 g |
| Hexyl cinnamic aldehyde, alpha | 7.5 g |
| Patchouly Oil Indonesian | 4.0 g |
| Iso-E ™ (b) | 2.0 g |
| Vetiveryl acetate | 2.0 g |
| Brahmanol ™ F (c) | 2.0 g |
| Benzyl Salicylate | 2.0 g |
| cis-3-Hexenyl Salicylate | 1.0 g |
| Cedramber ™ (b) | 1.0 g |
| Musk Xylene | 1.0 g |
| Indole 10% in DPG | 0.5 g |
| Extract of Opoponax | 0.5 g |
| Extract of Oakmoss 50% in DPG | 5.0 g |
| (a) Firmenich | |
| (b) IFF | |
| (c) DRAGOCO | |
| Total Parts by weight of First Premix: | 68.0 g |

The first perfume premix is modified by adding to it 32 parts by weight of 5a/5b (80:20) wherein 5a is 5-ethylenedioxy-3 beta-H-isolongifolane and 5b is 5-ethylenedioxy-3 alpha-H-isolongifolane; these two compounds being conventional perfume ketals not in accordance with the present invention, and their synthesis is described in "CYCLIC ISOLONGIFOLANONE-KETALS—THEIR MANUFACTURE AND THEIR APPLICATION", U.S. Pat. No. 5,426,095, issued Jun. 20, 1995 to Brunke and Schatkowski, assigned to Dragoco.

1.0 g of a pro-fragrance according to Example 2 is mixed into the powdered, perfume-free detergent composition. Finally, about 1.5 g of the above perfume composition is sprayed onto the mixture of detergent and pro-fragrance, to complete the fragrance, pro-fragrance laundry detergent composition. The said composition has a floral-woody character and leaves an improved, long-lasting scent on textile fabrics washed therewith.

Example 5
[Detergent having the form of a Laundry Bar Comprising Pro-Fragrance]

| | |
| --- | --- |
| Pro Fragrance of Example 1 | 1.0% |
| Tallow Soap and Coco Soap Mixture (80:20) | 44.0% |
| Linear Dodecyl Benzene Sulfonate | 12.0% |
| Sodium Tripolyphosphate | 6.0% |
| Sodium Carbonate | 8.0% |

| -continued | |
| --- | --- |
| Sodium Sulfate | 0.5% |
| Talc | 9.0% |
| Perfume*[1] | 0.2% |
| Moisture balance up to 100% | |

*[1]See *2 in Example 3

Example 6
[Liquid Detergent Comprising Pro-Fragrance]

| | |
| --- | --- |
| Pro Fragrance of Example 1 | 1.0% |
| Sodium C12–C15 Alcohol Ethoxylate E 2.5 Sulfate | 18.0% |
| Neodol 23-9 Nonionic surfactant | 2.0% |
| $C_{12}$ Alkyl N-Methylglucamide | 5.0% |
| Sodium Cumene Sulfonate | 3.0% |
| Citric Acid | 3.0% |
| Fatty Acid (C12–C14) | 2.0% |
| Boric Acid | 3.5% |
| Sodium Hydroxide | 2.8% |
| Ethoxylated Tetraethylene Pentaimine | 1.2% |
| Soil Release Polymer | 0.15% |
| 1,2-Propanediol | 8.0% |
| Ethanol | 3.6% |
| Monoethanolamine | 1.1% |
| Minors*[1] | 1.8% |
| Moisture balance up to 100% | |

*[1]Minors include brightner and enzymes

Although the examples and embodiments described herein are illustrative of the invention, those skilled in the art will be able to recognize that variations or modifications in light thereof are fully within the scope of the invention. In one such variation, the practioner will minimize the molecular weight while still seeking the advantages of the invention, for example by selecting pro-fragrances at-½ of less than one minute at pH 0.

What is claimed is:

1. An acetal or ketal pro-fragrance compound, said pro-fragrance formed from a corresponding aldehyde or ketone and one or more alcohols, wherein said aldehyde, ketone, or alcohol:

a) is a fragrance compound;

b) has a Clog P value of less than about 4; and said acetal or ketal pro-fragrance compound has:

a) a molecular weight of at least 170;

b) a $t_{1/2}$ of less than 60 minutes measured by the hydrolysis half-life test at pH 0.

2. A pro-fragrance compound according to claim 1 wherein said fragrance compound has a ClogP of less than 3.

3. A pro-fragrance compound according to claim 1 wherein said aldehyde or ketone which forms said pro-fragrance compound has a molecular weight of at least 80.

4. A pro-fragrance compound according to claim 1 wherein said pro-fragrance compound is in the form of a cyclic ketal and comprises at least 3 oxygen atoms.

5. A pro-fragrance compound according to claim 1 wherein said pro-fragrance compound has the formula:

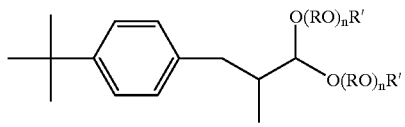

wherein each R is independently ethylene, propylene, and mixtures thereof; each R' is independently $C_6$–$C_{20}$ alkyl, n is from 1 to 30.

6. A pro-fragrance compound according to claim 5 wherein said pro-fragrance compound has the formula:

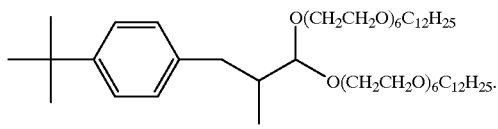

7. A pro-fragrance compound according to claim 5 wherein said pro-fragrance compound has the formula:

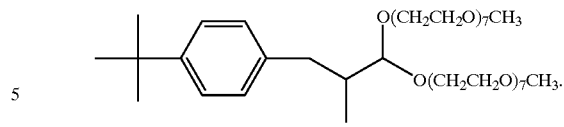

8. A pro-frauance compound according to claim 1 which is the reaction product of 2-octanone and an admixture of $C_{12}$–$C_{15}$ linear alkyl alcohols which are ethoxylated to an average of 6 ethoxy units per molecule.

9. A pro-fragrance compound according to claim 1 which is the reaction product of 2-octanone and polyethylene glycol methyl ether having an average molecular weight of about 300.

10. A pro-fragrance compound according to claim 1 which is the reaction product of 3-(4-tertbutylphenyl)-2-methylpropanal and tripropylene glycol.

11. A pro-fragrance compound according to claim 1 which is the reaction product of 2,4-dimethyl-cyclohex-3-en-1-al and tripropylene glycol.

* * * * *